United States Patent [19]
Porter et al.

[11] Patent Number: 6,146,899
[45] Date of Patent: Nov. 14, 2000

[54] HEIGHT REFERENCING BIOCHEMICAL CASSETTE

[75] Inventors: Marc D. Porter, Ames, Iowa; Vivian W. Jones, Woodbury, Minn.; Curtis L. Mosher; Eric Henderson, both of Ames, Iowa

[73] Assignee: Iowa State University Research Foundation, Inc., Ames, Iowa

[21] Appl. No.: 09/258,559

[22] Filed: Feb. 26, 1999

Related U.S. Application Data

[60] Provisional application No. 60/077,950, Mar. 13, 1998.
[51] Int. Cl.$^7$ .............................. C12Q 1/68; G01N 33/00
[52] U.S. Cl. .................................... 436/94; 435/6; 436/94
[58] Field of Search .................................... 436/94; 435/6

[56] References Cited

U.S. PATENT DOCUMENTS 5,514,501 5/1996 Tarlov .......................................... 430/5

OTHER PUBLICATIONS

Entering the Postgenome Era, Oct. 20, 1995, pp. 368–371.
Mark Schena, Dari Shalon, Ronald W. Davis, Patrick Brown; Quantitative Monitoring of Gene Expression Pattern with a Complementary DNA Microaray, 4 pages, Stanford, California.
William Bains, Jeffrey L. Fox, Litigation Escalates for Patents on a Chip; 2 Pages David Stipp, Gene Chip Breakthrough, 9 Pages.
Stephens P.A. Fodor, J. Leighton Read, Michael C. Pirrung, Lubert Stryer, Amy Tsai Lu, Dennis Solas; Light–Directed, Spatially Addressable Parallel Chemical Synthesis; Feb. 15, 1991, pp. 767–773; Palo Alto, California.
Ann Caviant Pease, Dennis Solas, Edward J. Sullivan, Maureen T. Cronin, Christopher P. Holmes and Stephen P.A. Fodor; Light–Generated Oligonucleotide Arrays for Rapid DNA Sequence Analysis; May 1994; pp. 5022–5026; Palo Alto, California.
Stephen P.A. Fodor, Richard P. Xiaohua C. Hunag, Ann C. Pease, Christopher P. Holmes and Cynthia L. Adams; Multiplexed Biochemical Assays with Biological Chips; p. 555.
Charles Y. Cho, Edmund J. Moran, Sara R. Cherry, James C. Stephans, Stephen P.A. Fodor, Cythia L. Adams, Arathi Sundaram, Jeffrey W. Jacobs, Peter G. Schultz; An Unnatural Biopolymer; Sep. 3, 1993; pp. 1303–1305; Palo Alto, Ca.
Alexander B. Chetverin, Fred Russell Kramer; Oligonucleotide Arrays: New Concepts and Possibilities; Nov. 12, 1994; pp. 1093–1099; Moscow Region, Russia and New York, New York.
Vivian W. Jones, Jeremy R. Kenseth, and Marc D. Porter; Microminiaturized Immunossays Using Atomic Force Microscopy and Compositionally Patterned Antigen Arrays; Feb. 26, 1998; pp. 1233–1241; Ames, Iowa.
Arjan P. Quist, Anna A. Bergman, Curt T. Reimann, Sven O. Oscarsson and Bo U.R. Sundqvist; Imaging of Single Antigens, Antibodies, and Specific Immunocomplex Formation by Scanning Force Microscopy; Jun. 28, 1995, pp. 395–400; Chicago, IL.
Oscar H. Willemsen, Margot M.E. Snel, Kees O. van der Werf, art G. de Grooth, Jan Greve, Peter Hinterdorfer, Hermann J. Gruber, Hansgeorg Schindler, Yvette van Kooyk, and Carl G. Figdor; Simultaneous Height and Adhesion Imaging of Antibody–Antigen Interactions by Atomic Force Microscopy; Nov. 1998; pp. 2220–2228; The Netherlands.
Vivian W. Jones, Jeremy R. Kenseth, Janese C. O'Brien, Marc D. Porter, Curtis L. Mosher and Eric Henderson; Orientationally Controlled Biomolecular Self–Assembly for Scanning Probe Bioassay Technologies; Mar. 1997, One page; Atlanta, Georgia.

*Primary Examiner*—John S. Brusca
*Assistant Examiner*—Jeffrey S. Lundgren
*Attorney, Agent, or Firm*—Zarley, McKee, Thomte, Voorhees & Sease

[57] ABSTRACT

A height referencing biochemical cassette comprising of a surface suitable to act as a coupling agent, a height referencing indicator, and molecules bonded to the surface. This cassette is a capable of use to test for bonding to these molecules through measuring the height difference between the indicator and the surface. This invention provides an efficient means to quickly and easily test for bonding of molecules to other molecules.

26 Claims, No Drawings

HEIGHT REFERENCING BIOCHEMICAL CASSETTE

CROSS-REFERENCE TO RELATED APPLICATION

This application is a continuation of co-pending, commonly owned United States provisional application Ser. No. 60/077,950 filed Mar. 13, 1998, entitled THE BIOCHEMICAL CASSETTE, AN ADDRESSABLE MACROMOLECULAR ARRAY, priority is claimed under 35 U.S.C. Section 120.

GRANT REFERENCE CLAUSE

This invention was funded in part by a grant from the National Science Foundation, grant number DBI 9601789. The government may have certain rights in this invention.

FIELD OF THE INVENTION

The present invention relates to a bio chip and a method of making said bio-chip and a method of using said bio-chip to test for binding via height measurements.

PROBLEMS IN THE ART

Immunoassays play a critical role in clinical pharmaceutical and environmental chemistries. Typically methodologies such as optical, amperometric, radiochemical, piezoelectric, and capacitive mechanisms are used to detect antigen-antibody binding. However, these methodologies generally require the use of labeled receptors, which adds several preparative steps to the overall assay. Other difficulties arise when using these other formats. For example, radiochemical immunoassays require stringent disposal procedures. Capacitive-based immunoassays provide performance challenges in regard to orientation control of an immobilized receptor and the construction of extremely thin insulating layers for enhancing sensitivity. Piezoelectric devices are currently limited from the orientation of immobilized receptors and the response of these devices in liquid environments.

Determination of adhesive strength bindings of antigen-antibody interactions by atomic force microscopy (AFM) are typically affected by non-specific interactions between a modified probe tip in the sample surface. Another methodology utilizing the AFM is topographic imaging. This approach relies on the change in the height that results from ligand-receptor binding and, therefore, does not require the use of labeled receptors. Generally height changes of 3–4 nanometers are observed as a consequence of absorption of antigenic IgG to a surface, followed by a similar increase upon antibody-antigen binding.

Therefore, it is a primary objective of the present invention to provide a new type of bio-chip, termed the biochemical cassette or biocassette, which overcomes or solves the problems and deficiencies in the art.

Another objective of the present invention is to provide a method of making the biochemical cassette.

A further objective of the present invention is to provide a biochemical cassette where large molecules can be deposited at micron sized addresses or even smaller.

Another objective of the present invention is to provide a biochemical cassette that is easy to manufacture.

Another objective of the present invention is to provide a biochemical cassette that may be easily measured to show topographic changes.

These and other features, objects, and advantages of the present invention will become apparent to those skilled in the art to reference to the specification and claims. The biochemical cassette is formed by placing a suitable coupling agent to the cassette surface. The molecules are bound to the surface.

Another embodiment is to provide a topographic point, plane, or array; which is suitable in use for height referencing.

A further embodiment is to place molecules of different compositions within the rows or arrays of the second embodiment.

An immunoassay can then be performed using this biocassette. An antibody may be bound as the molecule to the surface and topographis measurements are then taken. A change in height can be calculated from either prior measurements of the cassette to the exposure of the solution, or the differences in height as indicated between the reference point, plane, or arrays; and the height of the non-referencing surface following exposure of the solution. A change in height indicates the formation of an antigen-antibody pair. Similar types of analyses can be accomplished using the change in topology. For example, chemical systems should not be limited solely to biological systems.

SUMMARY OF THE INVENTION

A biochemical cassette, or biocassette can be easily manufactured and utilized by a topographical measurement to test for the bonding of molecules. A height referencing indicator allows for these measurements.

Immunoassays can be performed using this biocassette when bonding antibodies in known surface locations. These immunoassays may be selected from the groups of proteins, protein fragments, antibodies, antibody fragments, DNA, DNA oligomers, and other chemically selective proteins and nucleic acids. The surface is then exposed to a solution and measurements are taken to indicate bonding.

EXAMPLE OF AN EMBODIMENT

The preferred method for constructing the biochemical cassette is comprised of five steps. The first step is the fabrication of the gold substrate. Besides gold, the surface of the biocassette may also be comprised of silicon, silver, platinum, carbon, copper, or mica. Namely, the surface must be solid and capable of being made smooth. The gold substrate fabrication utilizes 10 mm×10 mm silicon wafers ((111) single crystals, manufactured by Montco Silicon). Other highly polished substrates work well. The silicon wafers are precleaned in an ultrasonic bath for 30 minutes in water and 30 minutes in ethanol. Next, the substrate is removed from the solution, dried using high-purity argon (available from Air Products) and placed in a vacuum evaporator (manufactured by Edwards). The substrate is then primed with a thin layer (15 nm) of chromium, at a rate of 0.1 nm/s, followed by the deposition of 300 nm of gold (99.99% purity), at a rate of 0.3–0.4 nm/s. The gold coated substrate is either used immediately upon removal from the evaporator, or stored under dry nitrogen.

After fabricating the gold substrate, the second step involves the formation of the octadecanethiol (ODT) derived monolayer. Other coatings that have low affinities to non-specific absorption, such as fluorinated coating (e.g. PTFE) work well. The monolayer is formed by immersing the gold-coated substrates into dilute (1–10 mM) ethanolic solutions of recrystalized ODT (produced by Aldrich) for approximately 24 hours. These samples are then rinsed extensively with ethanol (manufactured by Quantum, punctilious grade) and dried under a stream of argon.

The third step utilizes a patterning process. Mechanical, chemical, and wet etching can accomplish this step. In this example, photopatterning is used. This process has been previously described in Tarlov, et al., *Journal of the American Chemical Society* 1993, 115, 5305. The patterns can be created, as an example, by sandwiching a copper transmission electron microscopy (TEM) grid (2000 mesh (hole size 7.5 $\mu$m; bar size 5.0 $\mu$m))(manufactured by Electron Microscopy Sciences) between an ODT coated sample and a quartz plate. A 200-W, medium-pressure mercury lamp (manufactured by Oriel) is used as the light source. The light is collimated, reflected off an air-cooled, dichroic mirror (220–260 nm), focused by a fused-silica lens, and passed through the TEM grid before impinging onto the sample. The sample is irradiated for approximately 20 minutes, with the power at the sample estimated at 550 mW/cm$^2$. The photopatterning process converts the irradiated gold-bound thiolates to various forms of oxygenated sulfur (e.g., $RSO_3-$). This conversion was verified using X-ray photoelectron spectroscopy (XPS) and infrared reflection-absorption spectroscopy (IRRAS). The oxygenated forms of sulfur are readily removable by rinsing with most organic solvents. The use of AFM detected a height difference of approximately 2 nm between the ODT layer in the grids and the uncoated gold in the squares.

The fourth step entails removing the sulfonated part of the adlayer structure. In this example, it is done by rinsing with distilled, deionized water (produced by Millpore) and with ethanol. After drying under a stream of argon, the samples are immediately immersed into a dilute (0.1–1 mM) ethanolic solution of DSU [dithiobis(succinimidyl undecanoatte)] for approximately 12 hours. DSU serves as a coupling agent for linking and containing molecules, including IgG, to the surface. Any kind of coupling chemistry would be appropriate. For example, amine with antibodies, hydroxy groups, or carboxylic acids would be available. The coupling agent should be capable of immobilizing proteinaceous or proteinic materials on the surface. Under these conditions there was no detectable displacement of the ODT adlayer by solution-based DSU, as determined by IRRAS (detection limit, ~0.05 monolayer). The combination of steps 1–4 produces a compositionally patterned surface with the DSU adlayer confined in the squares and the ODT adlayer confined in the grids.

After steps 1–4 are completed, the presence of a compositional pattern on the surface, with a DSU adlayer confined in the squares, and an ODT adlayer confined in the grids, can be verified using AFM imaging. A Multimode Nanoscope III AFM (manufactured by Digital Instruments), equipped with a 150-$\mu$m tube scanner was used to obtain friction measurements of the surface. The friction image (60 $\mu$m×60 $\mu$m) was captured in a contact mode using 200 $\mu$m, oxide-sharpened, $Si_3N_4$ cantilevers (available from Nanoprobes) with normal bending and torsional force constants of approximately 0.06 and 80 N/m, respectively. The friction image was obtained with a load or normal force of approximately 25 nN while the AFM chamber was continuously purged with dry nitrogen.

The friction image showed a surface composed of a periodic array of squares and grids, the squares having a higher friction than the grids. The grids were approximately 5 $\mu$m wide, and the squares were approximately 7.5 $\mu$m wide, which are consistent with the photopatterning process described earlier. The difference between the friction of the squares and of the grids is consistent with the known difference between the friction of an ODT layer and the friction of a DSU layer.

Once the compositionally patterned surface (steps 1–4) is formed, the fifth and final step consists of covalent immobilization of rabbit IgG. Polyclonal rabbit IgG (manufactured by Pierce) is used. Covalent immobilization is achieved by immersing the compositionally patterned samples into a 50 mM Delbucco's phosphate buffer (PBS) (available from Life Technologies) at a pH of 6.0 with the addition of 1% (v/v) Tween®80 (polyethylenesorbitan monooleate) (manufactured by Aldrich) and 1 mg/mL antibody. Tween®80 minimizes nonspecific binding of IgG onto the surface. The acyl carbon of the succinimidyl ester group of DSU is very susceptible to nucleophilic attack by primary amine-containing compounds (i.e., lysine residues of a protein), resulting in the formation of an amide linkage. The large number of lysine residues that are distributed throughout the IgG structure lead to its bonding with DSU, immobilizing the IgG.

Both AFM imaging and fluorescent imaging were used to ensure that a spatially patterned array of immobilized rabbit IgG had been formed. An AFM topographic image and a friction image (both 40 $\mu$m×40 $\mu$m) of a patterned surface that had been formed using steps 1–5 were acquired under dry nitrogen at a load or normal force of approximately 2 nN. The height of the rabbit IgG adlayer in the squares was 3–4 nm larger than the ODT adlayer in the grids. This height differential indicates a successful creation of a patterned array of antibodies. The difference in friction was also consistent with the expected differences in the composition of the two components for the patterned surface.

Fluorescent images were acquired using an Odyssey confocal scanning laser microscope (manufactured by Noran Instruments) in combination with an Axiovert 135 inverted microscope (produced by Zeiss). Solutions containing goat anti-rabbit IgG and goat anti-bovine IgG samples were used in the fluorescent images. These solutions contained 0.1 mg/mL of the particular antibody in a "binding buffer" composed of 100 mM Tris-HCl (pH 7.6), 100 mM NaCl, 15 mM magnesium chloride, and 1% (v/v) Tween 80. Other compositions of a binding buffer can also be used. Any solution required to get binding to work would be appropriate. The goat anti-rabbit and goat anti-bovine IgG were conjugated with fluorescein isothiocyanate (FITC). All of the reagents are manufactured by Sigma.

For the fluorescence experiments, the immobilized rabbit IgG arrays were incubated in binding buffer containing the FITC-tagged secondary antibody for approximately 12 hours. After being removed from the buffer solution, the samples were rinsed with copius amounts of deionized water and dried under a stream of argon. The samples were protected from light during all preparation steps prior to imaging. The images were acquired using samples immersed in deionized water. Image collection followed a two-step process. First, bright-field images were acquired to establish a focal plane on the sample surface to minimize sample photobleaching. Second, 16 confocal fluorescence images were collected and averaged using 488-nm excitation a 515-nm low-pass barrier filter (rejection at 488 nm, $4 \times 10^{-4}$), and a 25 $\mu$m slit width.

The fluorescent image of the immobilized rabbit IgG that was incubated with the goat anti-rabbit antibody tagged with FITC exhibited a pattern of fluorescent 7.5 $\mu$m squares separated by nonfluorescent grids. This image indicates that step 5 results in the immobilization of an array of viable rabbit IgG and that there is no nonspecific adsorption of the FITC-tagged antibody on the grids. The lack of nonspecific adsorption on the grids is attributable to the presence of the Tween 80 surfactant in the buffer solution along with the hydrophobicity of ODT. The absence of nonspecific adsorption allows the adlayer to serve as an internal reference plane for measuring height changes.

A fluorescent image of an immobilized array of rabbit IgG that had been exposed to the goat anti-bovine secondary antibody tagged with FITC was also obtained. The fluorescent image appeared dark under the same illumination conditions that were used to view the other fluorescent image. This indicates a lack of any detectable nonspecific adsorption of the goat anti-bovine IgG at the patterned array. The two images together support the construction of a viable, compositionally patterned array of covalently immobilized rabbit IgG antibodies that can be utilized for an AFM-based immunoassay.

An AFM height image (40 $\mu$m×40 $\mu$m) of a rabbit IgG array in 50 mM PBS and 1% (v/v) Tween 80 was obtained. This image was compared to an AFM height image obtained of the patterned array of rabbit IgG that was exposed to a solution containing 0.1 mg/mL goat anti-rabbit IgG in binding buffer composed of 100 mM Tris-HCl (pH 7.6), 100 mM NaCl, 15 mM magnesium chloride, and 1% (v/v) Tween 80. Both images were obtain at a load or normal force of of approximately 2 nN. The comparison of the images showed that the height of the squares, measured relative to that of the ODT adlayer in the grids, effectively doubles upon the introduction of the solution containing the specific secondary antibody. In addition, real time monitoring shows that the height increase appears to be complete within 5 minutes, indicating that the binding between the immobilized antigen and solution based antibody occurs rapidly. Overall, these results are diagnostic of the rapid formation of complementary antigen-antibody pairs within each of the IgG modified elements of the array.

A third AFM height image, of an array of rabbit IgG that was exposed to a solution containing 0.1 mg/mL goat anti-bovine IgG in binding buffer composed of 100 mM Tris-HCl (pH 7.6), 100 mM NaCl, 15 mM magnesium chloride, and 1% (v/v) Tween 80, was also obtained. The height difference between the squares and the grids is indistinguishable before and after the exposure of the immobilized array of rabbit IgG to the solution of goat anti-bovine IgG. This image indicates that the height changes that were observed when the rabbit IgG array was exposed to the goat anti-rabbit IgG were due to specific binding and not nonspecific binding. The combined weight of the three AFM height images demonstrates the potential for microminiaturized immunoassays using AFM.

By depositing various antibodies at known locations on the biochemical cassette, large scale immunoassays could be performed in a short time period. A typical AFM can scan an area of more than 100 $\mu$m$^2$ in 1–5 minutes. Thus, for the biochemical cassette described here, with 5 $\mu$m squares and 2 $\mu$m wide grid bars, the AFM could interrogate approximately 200 individual addresses in a few minutes.

In addition to the above results, a preliminary study supports the possible regeneration and reuse of the biochemical cassette. The experiment was conducted by rinsing a rabbit IgG array that was coupled to goat anti-rabbit IgG with a solution of 100 mM glycine-HCl (pH 2.4). This processing effectively breaks the antigen-antibody pair and leaves the rabbit IgG array intact for potential reuse. Topographic imaging after exposure to the glycine-HCl solution showed the original rabbit IgG array was still present.

What is claimed is:

1. A biocassette, said biocassette providing an internal reference plane for the detection of topographic changes, formed by the process of:
    fabricating a surface that can be made smooth;
    patterning the surface to form a periodic array of coated surfaces and uncoated surfaces, whereby a hydrophobic monolayer is confined on the coated surfaces, said monolayer serving as a height referencing indicator;
    applying a coupling agent to the patterned surface to form an adlayer of coupling agent on the uncoated surfaces, said coupling agent being capable of immobilizing proteinaceous materials or nucleic acids; and
    immobilizing at least one protein or nucleic acid on the adlayer.

2. The biocassette of claim 1, wherein the protein or nucleic acid is selected from the group consisting of proteins, protein fragments, antibodies, antibody fragments, DNA, and nucleic acids.

3. The biocassette of claim 1, wherein the surface is selected from the group consisting of gold (Au), silicon (Si), silver (Ag), platinum (Pl), carbon (C), copper (Cu), and mica.

4. The biocassette of claim 1, where in the monolayer exhibits nonspecific absorption.

5. The biocassette of claim 1 wherein the monolayer comprises ODT.

6. The biocassette of claim 1 wherein the coupling agent is selected from the group consisting of DSU, amine with antibodies, hydroxy groups, and carboxylic acids.

7. The biocassette of claim 1 wherein the coupling agent is DSU.

8. The biocassette of claim 1 wherein the immobilizing step comprises immersing the patterned surface into a solution comprising a buffer and a surfactant.

9. The biocassette of claim 8 wherein the surfactant is polyethylenesorbitan monooleate.

10. A method of making a biocassette, said biocassette providing an internal reference plane for the detection of topographic changes, comprising:
    fabricating a surface that can be made smooth;
    patterning the surface to form a periodic array of coated surfaces and uncoated surfaces, whereby a hydrophobic monolayer is confined on the coated surfaces, said monolayer serving as a height referencing indicator;
    applying a coupling agent to the patterned surface to form an adlayer of coupling agent on the uncoated surfaces, said coupling agent being capable of immobilizing proteinaceous materials or nucleic acids; and
    immobilizing at least one protein or nucleic acid on the adlayer.

11. The method of claim 10, wherein the protein or nucleic acid is selected from the group consisting of proteins, protein fragments, antibodies, antibody fragments, DNA, and nucleic acids.

12. The method of claim 10, wherein the monolayer exhibits nonspecific absorption.

13. The method of claim 10, wherein the indicator comprises an array.

14. The method of claim 13, wherein the array is created via photopatterning.

15. The method of claim 10 wherein the surface is patterned using a method selected from the group consisting of mechanical, chemical, and wet etching.

16. A biocassette, said biocassette providing an internal reference plane for the detection of topographic changes, comprising:

a surface patterned to form a periodic array of coated surfaces and uncoated surfaces, whereby a hydrophobic monolayer is confined on the coated surfaces, said monolayer serving as a height referencing indicator;

an adlayer of coupling agent on the uncoated surfaces, said coupling agent being capable of immobilizing proteinaceous materials or nucleic acids; and at least one immobilized protein or nucleic acid on the adlayer.

17. The biocassette of claim 16, wherein the protein or nucleic acid is selected from the group consisting of proteins, protein fragments, antibodies, antibody fragments, DNA, and nucleic acids.

18. The biocassette of claim 16, wherein the surface is selected from the group consisting of gold (Au), silicon (Si), silver (Ag), platinum (Pl), carbon (C), copper (Cu), and mica.

19. The biocassette of claim 16, where in the monolayer exhibits nonspecific absorption.

20. The biocassette of claim 16 wherein the monolayer comprises ODT.

21. The biocassette of claim 16 wherein the coupling agent is selected from the group consisting of DSU, amine with antibodies, hydroxy groups, and carboxylic acids.

22. The biocassette of claim 16 wherein the surface is gold.

23. The biocassette of claim 16 wherein the uncoated surfaces have a higher friction than the coated surfaces.

24. A biocassette, said biocassette providing an internal reference plane for the detection of topographic changes, comprising:

a surface patterned to form a periodic array of coated surfaces and uncoated surfaces, whereby an ODT monolayer is confined on the coated surfaces, said monolayer serving as a height referencing indicator;

an adlayer of DSU on the uncoated surfaces; and at least one immobilized protein or nucleic acid on the adlayer.

25. A method of making a biocassette, said biocassette providing an internal reference plane for the detection of topographic changes, comprising:

fabricating a surface that can be made smooth;

patterning the surface to form a periodic array of coated surfaces and uncoated surfaces, whereby an ODT monolayer is confined on the coated surfaces, said monolayer serving as a height referencing indicator;

applying DSU to the patterned surface to form an adlayer of coupling agent on the uncoated surfaces, said coupling agent being capable of immobilizing proteinaceous materials or nucleic acids; and immersing the patterned surface with the adlayer of coupling agent into a buffer solution comprising a protein or nucleic acid and a surfactant.

26. The method of claim 25 wherein the surfactant is polyethylenesorbitan monooleate.

* * * * *